(12) United States Patent
Farin et al.

(10) Patent No.: US 7,815,638 B2
(45) Date of Patent: Oct. 19, 2010

(54) APPLICATOR FOR AN ELECTROSURGICAL INSTRUMENT

(75) Inventors: Guenter Farin, Tuebingen (DE); Klaus Fischer, Nagold (DE); Volker Bartel, Bodelshausen (DE)

(73) Assignee: ERBE Elektromedizin GmbH, Tuebingen (DE)

( * ) Notice: Subject to any disclaimer, the term of this patent is extended or adjusted under 35 U.S.C. 154(b) by 148 days.

(21) Appl. No.: 10/525,802

(22) PCT Filed: Aug. 4, 2003

(86) PCT No.: PCT/EP03/08617

§ 371 (c)(1),
(2), (4) Date: Jul. 18, 2005

(87) PCT Pub. No.: WO2004/021906

PCT Pub. Date: Mar. 18, 2004

(65) Prior Publication Data

US 2006/0122595 A1    Jun. 8, 2006

(30) Foreign Application Priority Data

Sep. 4, 2002    (DE) .............................. 102 40 847

(51) Int. Cl.
*A61B 18/14*    (2006.01)
(52) U.S. Cl. ......................................... 606/45; 606/41
(58) Field of Classification Search ............. 606/48–50, 606/32–41, 1, 43–46; 219/121.36; 128/203.27
See application file for complete search history.

(56) References Cited

U.S. PATENT DOCUMENTS

| | | | | |
|---|---|---|---|---|
| 4,711,238 A | * | 12/1987 | Cunningham | 606/79 |
| 4,781,175 A | * | 11/1988 | McGreevy et al. | 606/40 |
| 4,901,719 A | * | 2/1990 | Trenconsky et al. | 606/49 |
| 5,088,997 A | * | 2/1992 | Delahuerga et al. | 606/42 |
| 5,098,430 A | * | 3/1992 | Fleenor | 606/42 |
| 5,306,238 A | * | 4/1994 | Fleenor | 606/42 |
| 5,693,044 A | * | 12/1997 | Cosmescu | 606/42 |
| 5,836,897 A | * | 11/1998 | Sakurai et al. | 601/2 |
| 5,836,909 A | * | 11/1998 | Cosmescu | 604/35 |
| 6,142,995 A | * | 11/2000 | Cosmescu | 606/41 |

(Continued)

FOREIGN PATENT DOCUMENTS

DE    295 06 077    8/1996

(Continued)

*Primary Examiner*—Michael Peffley
*Assistant Examiner*—Victoria W Chen
(74) *Attorney, Agent, or Firm*—Dickstein Shapiro LLP

(57) ABSTRACT

An applicator for an electrosurgical instrument, alternatively for argon-plasma coagulation and cutting, also argon-supported. The applicator includes a gas and high frequency current terminal, a cutting electrode attached to a gas and high frequency current supply pipe, an insulating cap for detachably fastening the applicator on the instrument handle, and an insulating casing tube displaceable relative to the applicator common longitudinal axis for exposing or covering the cutting electrode and surrounding the gas and high frequency current supply pipe over a longitudinal section, and a collar or an external right-angle bend at the casing tube distal end. At least one radially surrounding gas-sealing inhibiting device is arranged between an inside of the casing tube and an outside of the gas and high frequency current supply pipe, allowing that a respective position be frictionally fixed at any location of the displacement path of the casing tube.

27 Claims, 1 Drawing Sheet

U.S. PATENT DOCUMENTS

| | | | |
|---|---|---|---|
| 6,149,648 A * | 11/2000 | Cosmescu | 606/42 |
| 6,391,027 B1 * | 5/2002 | Farin et al. | 606/45 |
| 6,475,215 B1 * | 11/2002 | Tanrisever | 606/45 |
| 6,491,690 B1 * | 12/2002 | Goble et al. | 606/41 |
| 6,558,383 B2 * | 5/2003 | Cunningham et al. | 606/41 |
| 6,602,249 B1 * | 8/2003 | Stoddard et al. | 606/45 |
| 6,679,880 B2 * | 1/2004 | Yang et al. | 606/41 |
| 6,780,184 B2 * | 8/2004 | Tanrisever | 606/45 |
| 6,958,063 B1 * | 10/2005 | Soll et al. | 606/41 |
| 7,004,939 B2 * | 2/2006 | Mackay | 606/40 |
| 2002/0022838 A1 * | 2/2002 | Cunningham et al. | 606/41 |
| 2002/0077611 A1 * | 6/2002 | von Dyck et al. | 604/333 |

FOREIGN PATENT DOCUMENTS

| | | |
|---|---|---|
| WO | 98 01075 | 1/1998 |

* cited by examiner

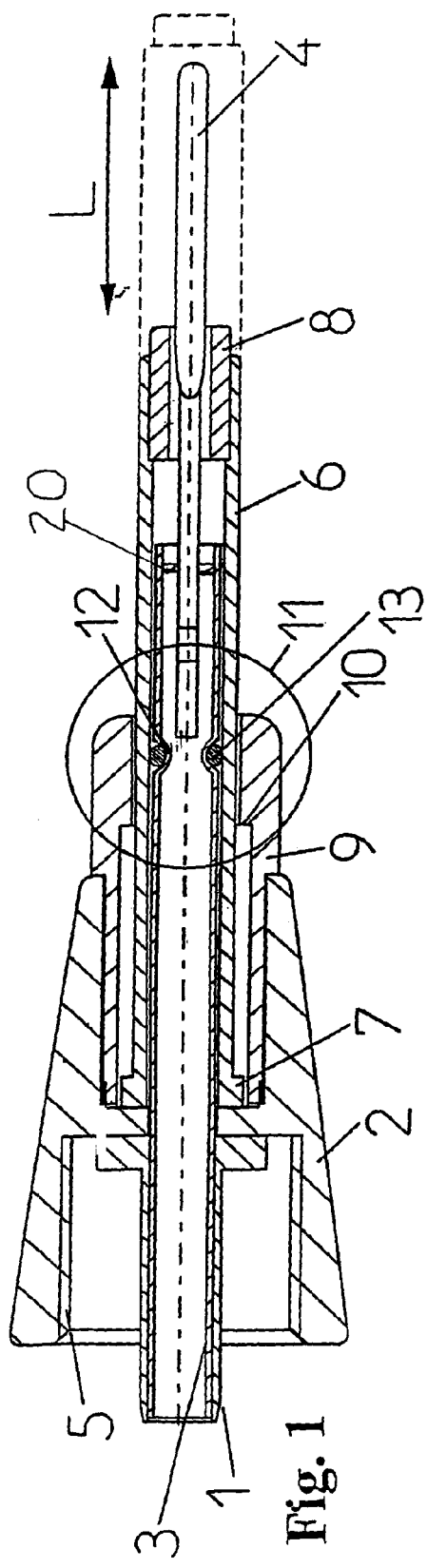
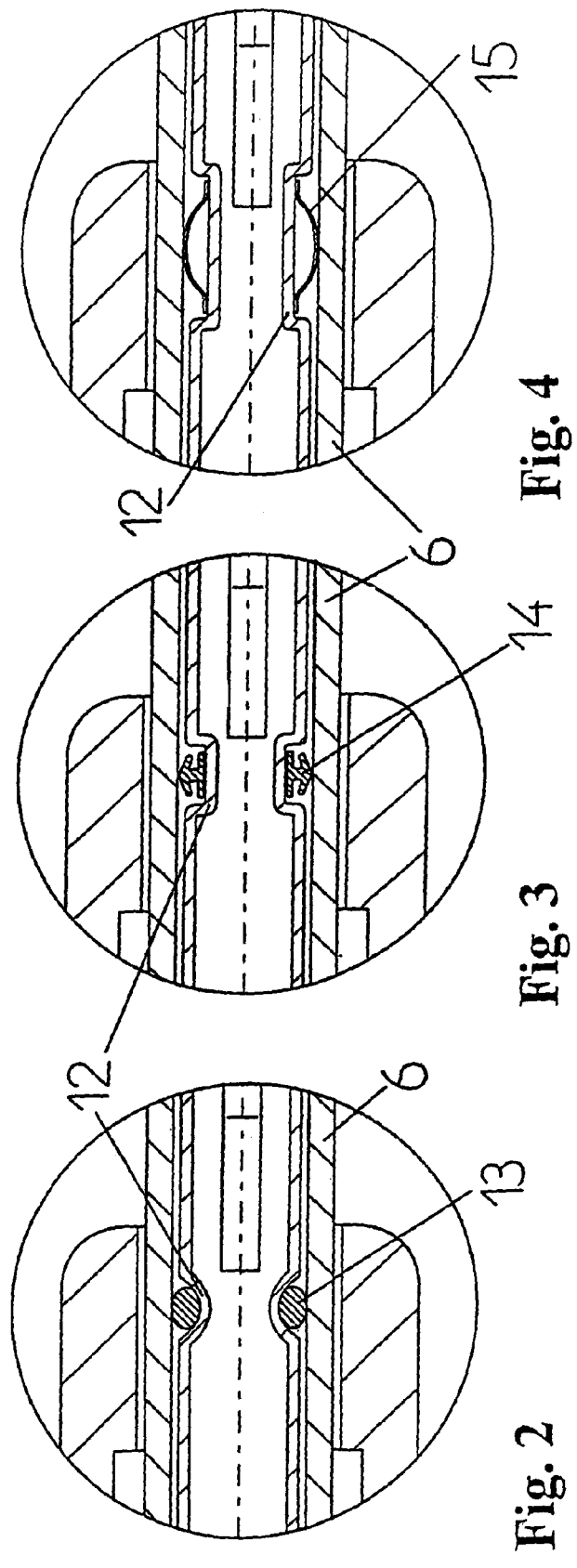

APPLICATOR FOR AN ELECTROSURGICAL INSTRUMENT

The invention relates to an applicator for an electrosurgical instrument, alternatively for argon-plasma coagulation as well as for cutting, also argon-supported.

U.S. Pat. No. 5,306,238 and the European Patent Document EP 0 604 539 B1, which forms part of the same patent family, disclose a laparoscopical electrosurgical pin. Said documents substantially describe an electrosurgical instrument with a handpiece, which allows two operating modes, namely the conventional electrical surgery and the gas-supported electrical surgery.

The solution described therein is to increase the safety of corresponding electrosurgical devices by reducing the probability of an accidental tissue puncture, especially when the device has to be introduced through narrow passages or is used in regions where the sight of the surgeon is limited. A drawback described in this respect is that a puncture with handpieces according to the prior art takes place if the exposed electrode is introduced too far through an access cannula.

Therefore, the cited patent documents relate to an electrosurgical instrument comprising a nozzle and an electrode, which have a common longitudinal axis, wherein the nozzle is arranged about at least a part of the electrode and gas can be supplied via the nozzle during the electrosurgical treatment. The aforementioned electrode supplies the necessary energy throughout the electrosurgical treatment. A shifting device is provided to adjust different longitudinal relationships between the nozzle and the electrode, with a front end of the electrode projecting out of a front end of the nozzle in a first position, and with the electrode being retracted in a second position. For facilitating the handling it is proposed to provide another device for retaining the corresponding structural components in the second position if an inactive state is prevailing, during which neither gas is supplied by the nozzle nor is electric energy applied to the electrode.

Hence, in connection with the solution according to EP 0 604 539 B1, it can be assumed that merely two actual positions can be adjusted, wherein the adjusting unit may also be operated in a spring-supported manner so as to obtain the desired final positions with an exposed or retracted electrode.

The gas-supported, axially displaceable surgical electrode disclosed in PCT/WO98/01075 is to facilitate the operation and the handling when the position of the electrode is to be adjusted relative to a casing tube. A movable grip and a handle are provided so as to displace the casing tube of the instrument or the electrode by a movement of the thumb in an axial direction, so that the electrode can be brought into an operating position or, respectively, that an APC mode can be adjusted. The electrode may automatically move back into the casing tube, e.g. by the influence of a spring force when a stop button is actuated or by laying down the instrument, or the casing tube may be brought into a position as to surround the electrode.

In an embodiment according to PCT/WO98/01075 the adjusting device is constructed such that the thread pitch of a female thread and a male thread relate to each such that the electrode can either be exposed or covered substantially by a quarter turn of the turning handle.

It is obvious from the total context of the cited teaching that the object thereof, too, is based on the adjustment of two desired final positions, namely the electrode either being exposed or retracted, all this with a possibly small amount of work involved.

It has shown, however, that it is problematical to realize the adjustments of screw threads since, apart from increased expenses and fabrication tolerances to be taken into account, they are not sufficiently gas-proof. The use of an instrument with a screw-shaped adjusting device bears the risk that the argon being a noble gas is electrically ionized in the screw-like construction and the columns and cavities provided therein and, consequently, becomes electrically conductive with the result that a high frequency current is able to flow in an uncontrolled manner. Therefore, additional sealing means would be required, which entail problems, however, in reusable instruments capable of being sterilized.

On the basis of the above it is, therefore, an object of the invention to provide a further developed applicator for an electrosurgical instrument, alternatively for argon-plasma coagulation as well as for cutting, also argon-supported, wherein the applicator is to be constructed such that an optional position of the electrode relative to a gas outlet nozzle can be adjusted, and wherein the respectively chosen position is not unintentionally changed when the instrument is used in accordance with its destination. Moreover, it is an object of the invention to construct the actual adjusting device or, respectively, the means as used in accordance with the invention such that sufficient impermeability to gas is ensured.

It basically must be avoided that the solution to be provided by an applicator for an electrosurgical instrument entails the risk that noble gas escapes inside the applicator or the instrument in an uncontrolled manner, where it is electrically ionized and forms a high frequency current flow that affects the performance of the applicator and thus results in operative risks.

Finally, the applicator is to be constructed in a cost-efficient manner so that it may also be applied for single-use purposes.

The applicator accordingly comprises a gas and high frequency current terminal known per se, a cutting electrode attached to a gas and high frequency current supply pipe, and an insulating cap for detachably fastening the applicator on a handle of the actual instrument.

Additionally provided is an insulating casing tube displaceable relative to the common longitudinal axis of the applicator for exposing or covering the cutting electrode, with the casing tube surrounding the gas and high frequency current supply pipe over a longitudinal section, and a collar or an external right-angle bend are provided at the distal end of the casing tube.

According to the invention at least one radially surrounding gas-sealing inhibiting device is arranged between the inside of the casing tube and the outside of the gas and high frequency current supply pipe, wherein the inhibiting device allows that the respective position be frictionally fixed at any location of the path of displacement of the casing tube.

According to an embodiment of the invention the collar or the external right-angle bend of the casing tube are provided with a groove which serves to accommodate another inhibiting device.

The inhibiting device is preferably located in the portion of a proximal extension of the insulating cap, wherein said proximal extension may be designed as a cap closing piece.

The actual path of displacement is defined by a hitting contact of the collar or the external right-angle bend on the casing tube with an inwardly projecting edge of the proximal extension of the cap, on the one hand, and with a portion for fastening the current supply pipe provided in the cap, on the other hand.

A consumption-resistant hollow cylindrical partially outwardly projecting insert, especially formed of ceramics, is arranged at the proximal outer end of the casing tube.

According to one realization alternative of the inhibiting device the current supply pipe has a radially surrounding groove or a corresponding notch on its outside, for accommodating e.g. a so-called O-ring, a profiled elastic sealing strip and/or a closed disk spring or leaf spring.

According to another embodiment the casing tube has an inwardly directed, radially surrounding groove or a corresponding notch for accommodating the inhibiting device.

The collar or the external right-angle bend at the distal end of the casing tube effect, in conjunction with a cylindrical inner recess of the cap extension, an additional radial and axial guidance for the casing tube, so that the distance of the electrode or, respectively, the coaxial alignment between the electrode and the casing tube are reproducible, if possible, and equal in each displacement position.

The insulating cap preferably has the shape of a truncated cone, with a hollow cylindrical recess of the upper surface of the truncated cone being provided at the outer end into which the already mentioned closing piece of the cap may be inserted. This closing piece of the cap forms the proximal extension of the cap.

At the outer end the closing piece of the cap has an internal collar for guiding the casing tube in a sliding manner.

The cutting electrode is preferably fastened at the proximal end of the inside of the gas and high frequency current supply pipe, wherein this fastening may be accomplished e.g. by spot-welding.

The cutting electrode may comprise a fastening support pipe at its distal end.

For obtaining a substantially coaxial position relative to the casing tube or the consumption-resistant insert, which forms a nozzle, the cutting electrode can be adjusted via the fastening support pipe for achieving an optimal surrounding gas flow in all cases in which the applicator is used.

The closing piece of the cap is integrally connected to the hollow cylindrical recess of the cap, preferably by gluing.

With respect to the assembly, the closing piece of the cap is pushed over the casing tube followed by the insertion of the closing piece of the cap into the aforementioned hollow cylindrical recess so as to achieve an integral connection.

According to the invention the gas and high frequency current supply pipe is therefore firmly connected to the cap, and a path of displacement is realized which may be defined by the closing piece of the cap and the internal collar provided thereon. The casing tube is then moved in correspondence with the desired path of displacement and is arrested by the inhibiting device in any optional position, so that a subsequent adjustment, also in the case of electrode consumption, may be accomplished in a simple manner.

For displacing the casing tube and for exposing or covering the electrode the applicator merely has to be gripped as to surround the same, wherein the casing tube can preferably be grasped with the thumb and the index so as to obtain the longitudinal displacement.

The static friction values are chosen such that the desired operation becomes possible with a normal strenuous effort and also when wearing surgical gloves.

The above description is based on an argon-plasma coagulation as a possible application for the applicator. However, also other noble gases, e.g. helium, may be used. The gas-proof inhibiting device prevents in any case that ionizable noble gas escapes in an uncontrolled manner and possibly streams into the interior of the applicator or the instrument itself. Thus, the inhibiting device as described fulfills a double function in terms of the necessary fixation of the casing tube relative to an electrode position and the striven for impermeability to gas.

The invention will hereinafter by explained in more detail by means of an embodiment in connection with figures.

FIG. 1 shows a sectional view through an applicator for an electrosurgical instrument, alternatively for argon-plasma coagulation as well as for cutting;

FIG. 2 shows a first embodiment of the inhibiting device;

FIG. 3 shows a second embodiment of the inhibiting device; and

FIG. 4 shows a third embodiment of the inhibiting device with a closed leaf spring.

The applicator according to FIG. 1 comprises a gas and high frequency current terminal 1 located in the center of an insulating cap 2.

In addition, a gas and high frequency current supply pipe 3 is provided, which extends from the terminal portion 1 through the entire assembly and forms a nozzle at the side of the exit. The gas and high frequency current supply pipe is formed of an electrically conductive material, e.g. stainless steel.

A cutting electrode 4 is held on the inside of the gas and high frequency current supply pipe 3, namely in the region of the external end, to which it is preferably welded.

The insulating cap 2 comprises an inside thread 5 for attaching the applicator on a handle (not shown) of the electrosurgical instrument.

An insulating casing tube 6 displaceable relative to the common longitudinal axis of the applicator allows the cutting electrode 4 to be exposed or covered, namely at an optional position over the path designated with L.

A collar or an external right-angle bend 7 are formed or provided at the distal end of the casing tube 6. Said collar or external right-angle bend 7 form a displacement stop and simultaneously serves to slidingly guide the casing tube 6 in the corresponding cap section.

A consumption-resistant hollow cylindrical, partially outwardly projecting ceramic insert 8 is disposed at the proximal outer end of the casing tube 6. This ceramic insert inhibits negative consumption occurrences caused by the plasma and prolongs the usability of the applicator.

The ceramic insert 8 additionally serves as gas outlet nozzle and may have, for this purpose, a corresponding inner formation, e.g. a conical shape.

According to the embodiment the insulating cap 2 has the shape of a truncated cone, wherein a hollow cylindrical recess is provided at the outer end of the cap 2 and a closing piece of the cap 9 can be inserted into said hollow cylindrical recess.

The closing piece of the cap 9 has an internal collar 10 at the outer end. This internal collar allows the sliding guidance and the positioning of the casing tube 6 and constitutes, in active communication with the collar 7 of the casing tube 6, an external stop.

As is shown in FIG. 1, at least one radially surrounding gas-proof inhibiting device 11 is disposed between the inside of the casing tube 6 and the outside of the gas and high frequency current supply pipe 3, wherein the inhibiting device 11 allows a frictional fixation of the respective position at each location of the path of displacement L of the casing tube 6.

Different embodiments of the inhibiting device 11 are illustrated in FIGS. 2 to 4.

According to FIG. 1, the inhibiting device 11 is preferably formed in the section of a proximal extension of the insulating cap 2, i.e. in the section of the closing piece of the cap 9.

As can be seen from the figure, the path of displacement L is defined by a hitting contact of the collar 7 with an inwardly projecting edge of the proximal extension of cap 2 and with a portion for the attachment of the current supply pipe 3 provided in cap 2.

According to FIGS. 2 to 3 the current supply pipe 3 comprises on its outside a radially surrounding groove 12, which serves to accommodate e.g. an O-ring 13 (FIG. 2), a profile packing 14 (FIG. 3) and/or a closed leaf spring 15 (FIG. 4).

It is, of course, in accordance with the invention to provide several O-rings 13 in an axially spaced apart manner, or to provide a double profile packing 14 so as to ensure an adjustment of the respective static friction forces for optimally holding and fixing the respectively displaced position. Also, it is possible to further develop the embodiment according to FIG. 4 with a closed leaf spring 15 such that a combination with an O-ring 13 may be made.

It is possible, kinematically reversed, that the casing tube comprises an inwardly directed, radially surrounding, groove or a corresponding notch for accommodating the inhibiting device, especially an O-ring.

Finally, it is also possible to provide a groove for accommodating an additional inhibiting device on the collar 7, wherein, here too, an elastic sealing ring is preferably used.

According to an embodiment of the invention the cutting electrode 4 is retained by a fastening support pipe 20 in the interior of the gas and high frequency current supply pipe 3. Said fastening support pipe, whereof the inner end is connected to the inside of the gas and high frequency current supply pipe e.g. by spot-welding, may, by bending, be adjusted in such a position that the cutting electrode adopts a substantially coaxial form relative to the ceramic insert 8, with the consequence that the escape of gas takes place in a steady and undisturbed manner.

In summary, the introduced applicator allows the active part of the cutting and/or coagulation electrode to move or project out of the casing tube more or less far in a defined manner, wherein the respective free electrode length may be chosen optionally and is arrested without any auxiliary means. Sufficiently stable arresting means that the respective length L cannot unintentionally be changed during the destined use of the instrument. Furthermore, the introduced embodiments relating to the inhibiting device provide for a sufficiently gas-proof construction of the applicator, so that the escape of noble gas and an uncontrolled high frequency current flow are avoided. Finally, with the solution as provided, a corresponding instrument may be manufactured in a cost-efficient manner, which is an advantage especially for devices which cannot be sterilized a second time.

| List of Reference Numerals | |
| --- | --- |
| 1 | gas and high frequency current terminal |
| 2 | cap |
| 3 | gas and high frequency current supply pipe |
| 4 | cutting electrode |
| 5 | inside thread of the cap |
| 6 | casing tube |
| 7 | collar or external right-angle bend of the casing tube |
| 8 | ceramic insert |
| 9 | closing piece of the cap |
| 10 | internal collar in the closing piece of the cap |
| 11 | inhibiting device |
| 12 | radially surrounding groove on the gas and high frequency current supply pipe |
| 13 | O-ring |
| 14 | profile packing |

| -continued | |
| --- | --- |
| List of Reference Numerals | |
| 15 | closed leaf spring |
| L | path of displacement |

The invention claimed is:

1. An applicator for an electrosurgical instrument, comprising:
   a gas and high frequency current terminal at a first end of said applicator;
   a cutting electrode at a second end of said applicator, opposite said first end;
   a gas and high frequency current supply pipe formed of an electrically conductive material and attached to said cutting electrode, said pipe forming a passage that communicates a gas from said gas and high frequency current terminal to a location proximate to said cutting electrode, said electrically conductive material of said pipe conducting a high frequency current that drives said cutting electrode from said gas and high frequency current terminal to said cutting electrode;
   an insulating cap having a cylindrical inner recess configured to detachably fasten the applicator on a handle of the instrument, the insulating cap having an annular protrusion that contacts a portion of the supply pipe to secure the supply pipe to the insulating cap, the insulating cap further having a proximal extension that surrounds the supply pipe, the extension extending away from the annular protrusion toward the second end of the applicator terminating with an inwardly projecting edge;
   an insulating casing tube surrounding a portion of the supply pipe and partially within the cap, the tube extending from the annular protrusion of the cap past the inwardly projecting edge of the cap, the tube having a collar on a tube end proximate to the annular protrusion, the tube displaceable along a longitudinal axis of the applicator, a path of displacement of the tube end with the collar being only between the annular protrusion of the cap and the inwardly projecting edge of the cap, so that the insulating tube can expose or cover the cutting electrode; and
   at least one radially surrounding gas-sealing inhibiting device arranged between an inside of the casing tube and an outside of the gas and high frequency current supply pipe, wherein the inhibiting device allows that a respective position be frictionally fixed at any location of the path of displacement of the casing tube, wherein
   said inhibiting device is adapted and arranged to prevent leakage of gas.

2. The applicator according to claim 1, wherein the inhibiting device is located in a portion of said proximal extension of the insulating cap.

3. An applicator according to claim 1, further comprising a consumption-resistant hollow cylindrical, partially outwardly projecting insert arranged at a proximal outer end of the casing tube.

4. An applicator according to claim 1, wherein the current supply pipe includes a radially surrounding groove or a corresponding notch on its outside for accommodating the inhibiting device.

5. An applicator according to claim 1, wherein the casing tube includes an inwardly directed, radially surrounding groove or a corresponding notch for accommodating the inhibiting device.

6. An applicator according to claim 1, wherein the inhibiting device comprises at least one of an O-ring, a profiled elastic sealing strip, and a closed leaf spring.

7. An applicator according to claim 1, wherein the collar of the casing tube effects, in conjunction with the cylindrical inner recess of the insulating cap extension, an additional radial and axial guidance for the casing tube.

8. An applicator according to claim 1, wherein the collar external right-angle bend comprises a groove for accommodating an additional inhibiting device.

9. An applicator according to claim 8, wherein the additional inhibiting device includes an elastic sealing ring.

10. An applicator according to claim 1, wherein the insulating cap has a shape of a truncated cone, with a cap closing piece being inserted into a hollow cylindrical recess of an upper surface of the truncated cone.

11. An applicator according to claim 10, wherein the cap closing piece forms the proximal extension of the insulating cap.

12. An applicator according to claim 10, wherein the cap closing piece includes an internal collar at an outer end.

13. An applicator according to claim 10, wherein the distal end of the casing tube is guided and retained by the cap closing piece.

14. An applicator according to claim 3, wherein the consumption-resistant insert is made of ceramics.

15. An applicator according to claim 1, wherein the cutting electrode is attached at a proximal end of an inside of the gas and high frequency current supply pipe.

16. An applicator according to claim 15, wherein the cutting electrode comprises a fastening support at its distal end.

17. An applicator according to claim 16, wherein the cutting electrode can be adjusted via a fastening support pipe for obtaining a substantially coaxial position relative to the casing tube or a consumption-resistant insert, for achieving an optimal surrounding gas flow in all cases in which the applicator is used.

18. An applicator according to claim 10, wherein the cap closing piece is integrally connected to the hollow cylindrical recess of the cap.

19. An applicator for an electrosurgical instrument, comprising:
a supply pipe formed of an electrically conductive material having a first and second end;
an electrode attached to said first end of said supply pipe;
an insulating member configured and adapted to surround a longitudinal section of said supply pipe, a first insulating member end adapted to be displaceable so as to extend past said first end of said supply pipe and a second insulating member end opposite said first insulating member end having a collar;
an insulating cap having a cylindrical inner recess surrounding a portion of said supply pipe and a portion of said insulating member, said cap having an annular protrusion in contact with said supply pipe to secure said supply pipe to said insulating cap, a cap end that extends toward said first end of said supply pipe having an inwardly projecting edge, said cap configured to detachably fasten the applicator on a handle of the instrument; and
a sealing member configured and adapted to provide a seal between an outer circumference of said supply pipe and an inner circumference of said insulating member, wherein said pipe forming a passage that communicates a gas flow;
said electrically conductive material of said pipe conducts a high frequency current that drives said electrode;
said insulating member is configured and adapted for displacement relative to said supply pipe in the direction of a longitudinal axis of said supply pipe, wherein a path of displacement of said second insulating member end with said collar being only between said annular protrusion of the cap and said inwardly projecting edge of said cap,
said sealing member is configured and adapted to frictionally fix said insulating member relative to said supply pipe,
said sealing member is adapted and arranged to prevent leakage of gas.

20. The applicator of claim 19, wherein said insulating member is an insulating tube configured for sliding engagement with an outer circumference of said supply pipe.

21. The applicator of claim 19, wherein said seal is a fluid-proof seal.

22. The applicator of claim 19, wherein said supply pipe extends through said insulating cap for communicating said gas flow and said high frequency current through said insulating cap.

23. The applicator of claim 19, wherein said electrode is attached to said supply pipe via an inner surface of said supply pipe.

24. An applicator for an electrosurgical instrument, comprising:
an insulating cap having a cylindrical inner recess, the cap having a first cap end and a second cap end, the second end having an edge that extends into the cylindrical recess;
a supply pipe formed of an electrically conductive material extending through the cap and past the first and second cap ends, the cap having an inwardly annular protrusion that contacts the pipe and secures the pipe within the cylindrical recess of the cap;
an electrode in electrical contact and secured to the supply pipe, the electrode extending away from the supply pipe and the second end of the cap;
an insulating tube surrounding a portion of the pipe, the tube surrounding the portion of the pipe extending from the annular protrusion of the cap past the second cap end, the tube having an outwardly extending collar on a tube end most proximate to the annular protrusion of the cap and within the cylindrical recess of the cap, wherein the tube is displaceable along a longitudinal axis of the pipe, a path of displacement of the tube end with the collar being only between the annular protrusion of the cap and the inwardly projecting edge of the cap; and
a gas-sealing device completely surrounding a portion of the pipe and in contact with the pipe and the insulating tube, wherein the applicator supplies a gas through the supply pipe to a location proximate to the electrode and the applicator supplies electric current through the supply pipe to the electrode.

25. The applicator of claim 24, wherein the tube is displaced to expose or cover the electrode.

26. The applicator of claim 24, wherein the tube is frictionally fixed along any point of the path of displacement.

27. The applicator of claim 24, wherein tube collar contacts the annular protrusion and the inwardly projecting edge of the cap thereby defining the path of displacement.

* * * * *